United States Patent [19]

Terrett

[11] Patent Number: 5,734,053

[45] Date of Patent: Mar. 31, 1998

[54] PURINONE ANTIANGINAL AGENTS

[75] Inventor: Nicholas Kenneth Terrett, Sandwich, United Kingdom

[73] Assignee: Pfizer Inc, New York, N.Y.

[21] Appl. No.: 726,886

[22] Filed: Oct. 4, 1996

Related U.S. Application Data

[63] Continuation of Ser. No. 356,196, filed as PCT/EP93/01561, Jun. 18, 1993, published as WO94/00453, Jan. 6, 1994, abandoned.

[30] Foreign Application Priority Data

Jun. 26, 1992 [GB] United Kingdom ............ 9213623

[51] Int. Cl.⁶ ..................... A61K 31/52; C07D 473/30
[52] U.S. Cl. ..................... 544/277; 544/118; 544/265
[58] Field of Search ........................ 544/265, 277, 544/118; 514/262, 234.2

[56] References Cited

U.S. PATENT DOCUMENTS 2,705,715  4/1955  Baker .................... 544/276
5,073,559  12/1991  Coates ................... 544/265

FOREIGN PATENT DOCUMENTS 0293063  11/1988  European Pat. Off. .
0347146  12/1989  European Pat. Off. .
0352960   1/1990  European Pat. Off. .
1338235  11/1974  United Kingdom .

OTHER PUBLICATIONS

Morrison and Boyd, *Organic Chemistry*, 858–859 (Allyn & Bacon 3rd Ed.) (1972).

Goodman and Gilman, *The Pharmacological Basis of Therapeutics*, 34 (Ed. Gilman, Rall, Nies and Taylor; McGraw Hill 8th Ed.)(1990).

*Primary Examiner*—Mark L. Berch
*Attorney, Agent, or Firm*—Peter C. Richardson; Paul H. Ginsburg; Garth Butterfield

[57] ABSTRACT

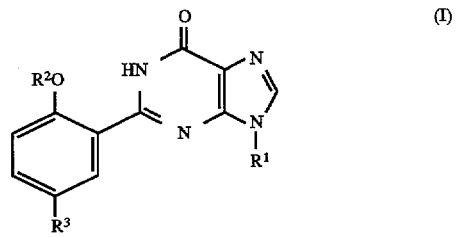

Compounds of formula (I), and pharmaceutically acceptable salts thereof, wherein $R^1$ is $C_1$–$C_4$ alkyl; $R^2$ is $C_2$–$C_4$ alkyl; $R^3$ is H or $SO_2NR^4R^5$; $R^4$ and $R^5$ together with the nitrogen atom to which they are attached form a pyrrolidino, piperidino, morpholino or 4-N-($R^6$)-1-piperazinyl group; and $R^6$ is H or $C_1$–$C_3$ alkyl; are selective cGMP PDE inhibitors useful in the treatment of, inter alia, cardiovascular disorders such as angina, hypertension, heart failure and atherosclerosis.

4 Claims, No Drawings

PURINONE ANTIANGINAL AGENTS

This is a continuation of application Ser. No. 08/356,196, filed as PCT/EP93/01561, Jun. 18, 1993 published as WO94/00453, Jan. 6, 1994.

This invention relates to a series of purin-6-ones, which are potent and selective inhibitors of cyclic guanosine 3',5'-monophosphate phosphodiesterase (cGMP PDE), having utility in a variety of therapeutic areas including the treatment of cardiovascular disorders such as angina, hypertension, heart failure and atherosclerosis.

The compounds of the invention exhibit selectivity for inhibition of cGMP PDEs rather than cyclic adenosine 3',5'-monophosphate phosphodiesterases (cAMP PDEs) and, as a consequence of this selective PDE inhibition, cGMP levels are elevated, which in turn can give rise to beneficial anti-platelet, anti-neutrophil, anti-vasospastic and vasodilatory activity, as well as potentiation of the effects of endothelium-derived relaxing factor (EDRF) and nitrovasodilators. Thus the compounds have utility in the treatment of a number of disorders, including stable, unstable and variant (Prinzmetal) angina, hypertension, pulmonary hypertension, congestive heart failure, atherosclerosis, conditions of reduced blood vessel patency e.g. postpercutaneous transluminal coronary angioplasty (post-PTCA), peripheral vascular disease, stroke, bronchitis, allergic asthma, chronic asthma, allergic rhinitis, glaucoma, and diseases characterised by disorders of gut motility, e.g. irritable bowel syndrome (IBS).

Australian patent application AU-A-10956/88 and European patent application EP-A-0352960 disclose certain purin-6-ones which, unlike the compounds of the present invention, are N-unsubstituted in the imidazole portion of the purinone bicyclic system. These prior art purinones are reported to be selective cGMP PDE inhibitors with bronchodilator and vasodilator activity, of value in combatting asthma, bronchitis, angina, hypertension and congestive heart failure. However, compared with the 9-alkylpurin-6-ones of the present invention, they are not particularly potent cGMP PDE inhibitors.

The compounds of the present invention have the formula (I):

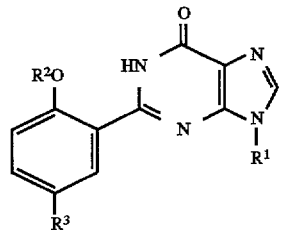

and pharmaceutically acceptable salts thereof, wherein
$R^1$ is $C_1$–$C_4$ alkyl;
$R^2$ is $C_2$–$C_4$ alkyl;
$R^3$ is H or $SO_2NR^4R^5$;
$R^4$ and $R^5$ together with the nitrogen atom to which they are attached form a pyrrolidino, piperidino, morpholino or 4-N-($R^6$)-1-piperazinyl group;
and $R^6$ is H or $C_1$–$C_3$ alkyl.

In the above definition, unless otherwise indicated, alkyl groups having three or more carbon atoms may be straight chain or branched chain.

The compounds of formula (I) may contain one or more asymmetric centres and thus they can exist as stereoisomers, i.e. as enantiomers or as diastereoisomers. The invention includes both mixtures thereof and the separated individual stereoisomers.

The compounds of formula (I) may also exist in tautomeric forms and the invention includes both mixtures thereof and the separated individual tautomers.

Also included in the invention are radiolabelled derivatives of compounds of formula (I) which are suitable for biological studies.

The pharmaceutically acceptable salts of the compounds of formula (I) are, for example, non-toxic acid addition salts formed with inorganic acids such as hydrochloric, hydrobromic, sulphuric and phosphoric acid, with organo-carboxylic acids, or with organo-sulphonic acids. Compounds of formula (I) can also provide pharmaceutically acceptable metal salts, in particular non-toxic alkali metal salts, with bases. Examples include the sodium and potassium salts. For a review on suitable pharmaceutical salts, see J. Pharm. Sci., 1977, 66, 1.

A preferred group of compounds of formula (I) is that wherein $R^1$ and $R^2$ are each independently ethyl or n-propyl; $R^4$ and $R^5$ together with the nitrogen atom to which they are attached form a 4-N-($R^6$)-1-piperazinyl group; and $R^3$ and $R^6$ are as previously defined.

A particularly preferred group of compounds of formula (I) is that wherein $R^1$ is n-propyl; $R^2$ is ethyl; and $R^3$ is 1-piperazinylsulphonyl or 4-methyl-1-piperazinylsulphonyl.

In another aspect, the present invention provides processes for the preparation of compounds of formula (I) and pharmaceutically acceptable salts thereof, as hereinafter described.

(A) A compound of formula (I), wherein $R^3$ is $SO_2NR^4R^5$, may be obtained from a compound of formula (I) wherein $R^3$ is H, and $R^2$ and $R^3$ are as previously defined for formula (I). This can be achieved via the intermediacy of a sulphonyl halide of formula (II):

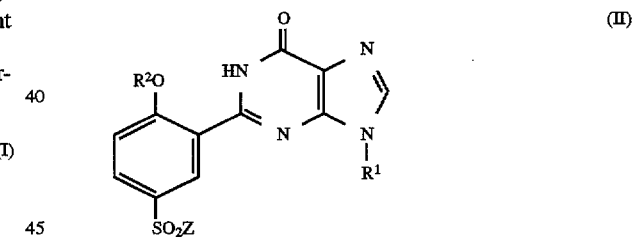

wherein Z is halo, preferably chloro, and $R^1$ and $R^2$ are as previously defined for formula (I), by reaction with an amine of formula (III):

wherein $R^4$ and $R^5$ are as previously defined for formula (I). The reaction is generally carried out at ambient temperature, preferably in the presence of a solvent, e.g. a $C_1$–$C_3$ alkanol, using about a 5-fold excess of (III) to scavenge the acid by-product (HZ) and, in the case of piperazine ($R^6$ is H), to minimise bis-sulphonamide formation.

A compound of formula (II) is obtainable by the application of known methods for the introduction of a $SO_2Z$ group into a benzene ring; for example, when Z is chloro, by the action of excess chlorosulphonic acid at from about 0° C. to about ambient temperature.

A compound of formula (I) wherein $R^3$ is H, $R^1$ and $R^2$ are as previously defined for formula (I), may be obtained from a compound of formula (IV):

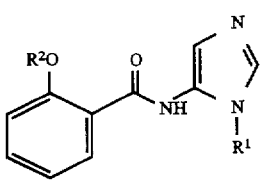

wherein $R^1$ and $R^2$ are as previously defined for formula (I), by the application of known cyclisation methods for pyrimidinone ring formation. Thus, for example, cyclisation may be effected by the treatment of (IV) with a base such as sodium hydroxide or potassium carbonate, optionally in the presence of excess hydrogen peroxide, in an ethanol-water medium, at about the reflux temperature of the reaction medium. Alternatively, cyclisation may be effected with polyphosphoric acid at about 140° C.

A compound of formula (IV) may be prepared from a compound of formula (V):

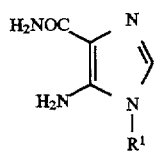

wherein $R^1$ is as previously defined for formula (IV), by reaction with an acyl halide of formula (VI):

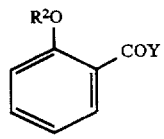

wherein Y is halo, preferably chloro or bromo, and $R^2$ is as previously defined for formula (IV). The reaction is generally carried out using from about 1 to about 2 equivalents of (VI) in the presence of an excess of a tertiary amine such as triethylamine or pyridine to act as scavenger for the acid by-product (HY), optionally in the presence of a catalyst such as 4-dimethylaminopyridine, in an inert solvent such as dichloromethane, at from about 0° C. to ambient temperature for 2–72 hours. For convenience, pyridine may also be used as solvent.

Alternative methods of converting (V) to a compound of formula (I) wherein $R^3$ is H, and $R^2$ and $R^3$ are as previously defined for formula (I), will be evident to persons skilled in the art. For example, a one-step procedure involves the reaction of (V) with an amidine of formula (VII):

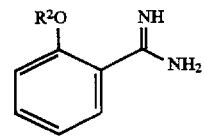

wherein $R^2$ is as previously defined for formula (I), at elevated temperature. The aminoimidazolecarboxamide component may be in the form of an acid addition salt, e.g. the hydrochloride, and the reaction may be conducted in the absence of solvent, or in a suitable solvent such as a $C_1$–$C_4$ alcohol, pyridine or N-methyl-pyrrolidone, at from about 65° C. to about 200° C.

A compound of formula (V) may be prepared from an amine of formula $R^1NH_2$ (VIII), wherein $R^1$ is as previously defined for formula (V), and 2-amino-2-cyanoacetamide in a two-stage process, according to the procedure disclosed in EP-A-66,909. Firstly, the latter component is condensed with a tri-lower alkyl orthoformate, e.g. trimethyl or triethylorthoformate, in a suitable solvent such as acetonitrile, at the reflux temperature of the reaction medium, then the intermediate formimidate is treated in situ with (VIII) at about ambient temperature. 2-Amino-2-cyanoacetamide can be obtained by dithionite reduction of ethyl 2-cyano-2-(hydroxyimino)acetate, followed by in situ amination of the intermediate ethyl 2-amino-2-cyanoacetate, as reported in Chem. and Ind., 1980, (13), 541.

(B) A compound of formula (I) wherein $R^3$ is $SO_2NR^4R^5$, may be obtained more directly from a compound of formula (V) by employing an acyl halide of formula (IX) or an amidine of formula (X):

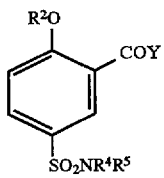

wherein $R^2$, $R^4$ and $R^5$ are as previously defined for formula (I) and Y is as previously defined for formula (VI), in reactions analogous to those described above for (VI) and (VII) respectively.

(C) A compound of formula (I) may also be obtained from the corresponding phenol precursor, i.e. a compound of formula (I) wherein $R^2$ is H and $R^1$ and $R^3$ are as previously defined for formula (I), thereby introducing $R^2$ at the final stage of the synthesis. This may be achieved by selective O-alkylation of the phenolic group under standard conditions, using the appropriate $C_2$–$C_4$ alkyl bromide, iodide or sulphonate, in the presence of a base such as anhydrous potassium carbonate, in a suitable solvent, e.g. 2-butanone, at from about ambient temperature to about the reflux temperature of the reaction medium. Alternatively, the alkylation may be effected under typical Mitsunobu reaction conditions. A variety of other selective O-alkylation procedures will be obvious to persons skilled in the art.

(D) Certain piperazines of formula (I), wherein $R^6$ is as previously defined for formula (I) but is not hydrogen, may be prepared directly from the corresponding 4-N-unsubstituted piperazine analogue, i.e. the precursor wherein $R^6$ is H, by standard alkylation procedures such as use of the appropriate $C_1$–$C_3$ alkyl bromide, iodide or sulphonate, in the presence of a base such as anhydrous potassium carbonate, in a suitable solvent, e.g. 2-butanone, at from about ambient temperature to about the reflux temperature of the reaction medium.

Compounds of formulae (VI), (VII), (IX) and (X), and the various reagents required for the processes hereinbefore disclosed, when neither commercially available nor subsequently described, can be obtained by conventional synthetic procedures, in accordance with standard textbooks on organic chemistry or literature precedent, from readily accessible starting materials using appropriate reagents and reaction conditions.

Moreover, persons skilled in the art will be aware of variations of, and alternatives to, those processes described hereinafter in the Examples and Preparations sections such that all the compounds defined by formula (I) are obtainable.

The pharmaceutically acceptable acid addition salts of the compounds of formula (I) which contain a basic centre may also be prepared in a conventional manner. For example a solution of the free base is treated with the appropriate acid, either neat or in a suitable solvent, and the resulting salt isolated either by filtration or by evaporation under vacuum of the reaction solvent. Pharmaceutically acceptable base addition salts can be obtained in an analogous manner by treating a solution of a compound of formula (I) with the appropriate base. Both types of salt may be formed or interconverted using ion-exchange resin techniques.

The biological activities of the compounds of the present invention were determined by the following test methods.

Phosphodiesterase activity

Compound affinities for cGMP and cAMP PDEs are assessed by determination of their $IC_{50}$ values (the concentration of inhibitor required for 50% inhibition of enzyme activity). The PDE enzymes are isolated from rabbit platelets and rat kidney, essentially by the method of W. J. Thompson et al. (Biochem., 1971, 10, 311). The calcium/calmodulin (Ca/CAM)-independent cGMP PDE and the cGMP-inhibited cAMP PDE enzymes are obtained from rabbit platelets whilst, of the four major PDE enzymes of the rat kidney, the Ca/CAM-dependent cGMP PDE (fraction I) is isolated. Assays are performed using a modification of the "batch" method of W. J. Thompson and M. M. Appleman (Biochem., 1979, 18, 5228). Results from these tests show that the compounds of the present invention are potent and selective inhibitors of both cGMP PDEs.

Platelet anti-aggregatory activity

This is assessed by the determination of a compound's ability to inhibit platelet aggregation in vitro induced by platelet activating factor (PAF), and to potentiate the platelet antiaggregatory action in vitro of activators of guanylate cyclase such as nitroprusside and EDRF. Washed platelets are prepared essentially by the method of J. F. Mustard et al. (Methods in Enzymol., 1989, 169, 3) and aggregation is determined using standard turbidimetric techniques as described by G. V. R. Born, (J. Physiol. (Lond), 1962, 162, 67P).

Antihypertensive activity

This is assessed following intravenous or oral administration of a compound to spontaneously hypertensive rats. Blood pressure is recorded via a cannula implanted in the carotid artery of either conscious or anaesthetised animals.

For administration to man in the curative or prophylactic treatment of angina, hypertension or congestive heart failure, oral dosages of the compounds will generally be in the range of from 4–800 mg daily for an average adult patient (70 kg). Thus for a typical adult patient, individual tablets or capsules contain from 2–400 mg of active compound, in a suitable pharmaceutically acceptable vehicle or carrier, for administration in single or multiple doses, once or several times per day. Dosages for intravenous, buccal or sublingual administration will typically be within the range of from 1–400 mg per single dose as required. In practice the physician will determine the actual dosing regimen which will be most suitable for an individual patient and it will vary with the age, weight and response of the particular patient. The above dosages are exemplary of the average case but there can be individual instances in which higher or lower dosage ranges may be merited, and such are within the scope of this invention.

For human use, the compounds of formula (I) can be administered alone, but will generally be administered in admixture with a pharmaceutical carrier selected with regard to the intended route of administration and standard pharmaceutical practice. For example, they may be administered orally, buccally or sublingually, in the form of tablets containing excipients such as starch or lactose, or in capsules or ovules either alone or in admixture with excipients, or in the form of elixirs or suspensions containing flavouring or colouring agents. The compounds may also be injected parenterally, for example intravenously, intramuscularly, subcutaneously or intracoronarily. For parenteral administration, they are best used in the form of a sterile aqueous solution which may contain other substances, for example salts, or monosaccharides such as mannitol or glucose, to make the solution isotonic with blood.

Thus the invention provides a pharmaceutical composition comprising a compound of formula (I), or a pharmaceutically acceptable salt thereof, together with a pharmaceutically acceptable diluent or carrier.

The invention also provides a compound of formula (I), or a pharmaceutically acceptable salt thereof, or a pharmaceutical composition containing either entity, for use in medicine.

The invention further provides the use of a compound of formula (I), or a pharmaceutically acceptable salt thereof, or a pharmaceutical composition containing either entity, for the manufacture of a medicament for the treatment of stable, unstable and variant (Prinzmetal) angina, hypertension, pulmonary hypertension, congestive heart. failure, atherosclerosis, stroke, peripheral vascular disease, conditions of reduced blood vessel patency, chronic asthma, bronchitis, allergic asthma, allergic rhinitis, glaucoma or diseases characterised by disorders of gut motility.

In a further aspect, the invention provides a method of treating or preventing stable, unstable and variant (Prinzmetal) angina, hypertension, pulmonary hypertension, congestive heart failure, atherosclerosis, stroke, peripheral vascular disease, conditions of reduced blood vessel patency, chronic asthma, bronchitis, allergic asthma, allergic rhinitis, glaucoma or diseases characterised by disorders of gut motility, in a mammal (including a human being), which comprises administering to said mammal a therapeutically effective amount of a compound of formula (I), or a pharmaceutically acceptable salt thereof, or a pharmaceutical composition containing either entity.

The invention also includes any novel intermediates of formulae (II) and (IV) disclosed herein.

The syntheses of the compounds of the invention and of the intermediates for use therein are illustrated by the following Examples and Preparations. The purity of the compounds was routinely monitored by thin layer chromatography (TLC) using Merck Kieselgel 60 $F_{254}$ plates. $^1$H-Nuclear magnetic resonance (NMR) spectra were recorded using either a Nicolet QE-300 or a Bruker AC-300 spectrometer and were in all cases consistent with the proposed structures.

Ambient temperature means 20°–25° C.

EXAMPLE 1

2-(2-Ethoxyphenyl)-9-n-propylpurin-6-one

A solution of 5-(2-ethoxybenzamido)-1-n-propylimidazole-4-carboxamide (Preparation 3; 0.35 g, 0.0011 mol) in ethanol (8 ml) was added to a stirred mixture of aqueous hydrogen peroxide (30% solution; 0.3 ml, 0.0026 mol), water (15 ml) and sodium hydroxide (0.2 g, 0.005 mol). The resulting mixture was heated at 90° C. for 7 hours, stirred at ambient temperature for a further 15 hours, then evaporated under vacuum. The residue was dissolved in water (20 ml), and the resulting solution acidified with hydrochloric acid to pH 4 and then extracted with dichloromethane (2 ×30ml). The combined organic extracts were washed with water (25 ml), dried (MgSO$_4$) and evaporated under vacuum to give the title compound, which crystallised from ethyl acetate as a colourless solid (0.17 g, 52%), m.p. 172°–174° C. Found: C,64.57; H,6.15; N,18.99. C$_{16}$H$_{18}$N$_4$O$_2$ requires C,64.41; H,6.08; N,18.78%.

EXAMPLE 2

2-[2-Ethoxy-5-(1-piperazinylsulphonyl)phenyl]-9-n-propylpurin-6-one 2-(2-Ethoxyphenyl)-9-n-propylpurin-6-one (0.5 g, 0.00167 mol) was added portionwise to ice-cold chlorosulphonic acid (3 ml) and the mixture stirred at ambient temperature for 15 hours. The resulting solution was added cautiously to stirred ice/water (50 g) and the mixture extracted with dichloromethane (2 ×50 ml). The combined organic extracts were dried (MgSO$_4$), then evaporated under vacuum to give 2-(5-chlorosulphonyl-2-ethoxyphenyl)-9-n-propylpurin-6-one (0.63 g) which was used without further purification.

A mixture of piperazine (0.36 g, 0.0041 mol), the preceding sulphonyl chloride (0.31 g, 0.00078 mol) and ethanol (15 ml) was stirred at ambient temperature for 15 hours, then evaporated under vacuum. The residue was chromatographed twice on silica gel (12 g) using a dichloromethane:methanol:aqueous ammonia elution gradient (95:5:0 to 90:10:0 to 90:10:1) to give the title compound, which crystallised from acetonitrile as a colourless hydrated solid (0.19 g, 55%), m.p. 174°–176° C. Found: C,53.22; H,6.08; N,18.56. C$_{20}$H$_{26}$N$_6$O$_4$S; 0.25 H$_2$O requires C,53.26; H,5.92; N,18.63%.

EXAMPLE 3

2-[2-Ethoxy-5-(4-methyl-1-piperazinylsulphonyl)phenyl]-9-n-propylpurin-6-one

The title compound was prepared from 2-(2-ethoxyphenyl)-9-n-propylpurin-6-one and 1-methylpiperazine, following the procedure of Example 2, and was obtained as a colourless solid (81%). m.p.—softens at 150° C. Found: C,54.94; H,6.30; N,17.92. C$_{21}$H$_{28}$N$_6$O$_4$S requires C,54.76; H,6.13; N,18.25%.

PREPARATION 1

2-Amino-2-cyanoacetamide

Ethyl 2-cyano-2-(hydroximino)acetate (30.0 g, 0.21 mol) was dissolved in a stirred mixture of saturated aqueous sodium bicarbonate solution (90 ml) and water (180 ml), and sodium dithionite (102 g, 0.59 mol) was then added portionwise. The resulting mixture was stirred at ambient temperature for 0.5 hour, then extracted with dichloromethane (4×200 ml). The organic extracts were combined, washed with saturated brine (200 ml), dried (Na$_2$SO$_4$) and evaporated under vacuum. The residue was stirred at ambient temperature for 1 hour with aqueous ammonia solution (SG 0.880, 250 ml) and, after cooling, the resulting solid was collected by filtration and dried under vacuum to give the title compound as a colourless solid (2.8 g, 13%), m.p. 123°–125° C. Rf 0.12 (SiO2; dichloromethane: methanol:aqueous ammonia, 90:10:1).

PREPARATION 2

5-Amino-1-n-propylimidazole-4-carboxamide

A mixture of 2-amino-2-cyanoacetamide (2.8 g, 0.0282 mol), trimethylorthoformate (3.4 g, 0.0321 mol) and acetonitrile (55 ml) was heated under reflux for 0.75 hour, then allowed to cool. n-Propylamine (1.8 g, 0.0305 mol) was then added dropwise, and the resulting mixture stirred at ambient temperature for 36 hours. The solid which precipitated was collected by filtration and crystallised from methanol to give the title compound as a colourless solid (2.9 g, 61%), m.p. 241°–243° C. Found: C,49.67; H,7.15; N,33.64. C$_7$H$_{12}$N$_4$O requires C,49.98; H,7.19; N,33.31%.

PREPARATION 3

5-(2-Ethoxybenzamido)-1-n-propylimidazole-4-carboxamide

Oxalyl chloride (1.74 g, 0.137 mol) was added dropwise to a stirred solution of 2-ethoxybenzoic acid (1.1 g, 0.00663 mol) and dimethylformamide (0.1 ml) in dichloromethane (20 ml) and the resulting mixture stirred at ambient temperature for 4 hours, then evaporated under vacuum. The residue was azeotroped with dichloromethane (2×20 ml), then added dropwise to a stirred solution of 5-amino-1-n-propylimidazole-4-carboxamide (0.9 g, 0.00536 mol) in pyridine (20 ml) The resulting solution was stirred at ambient temperature for 3 days, then evaporated under vacuum. The residue was dissolved in dichloromethane (50 ml), and the solution washed with 1N hydrochloric acid (30 ml), dried (Na$_2$SO$_4$) and evaporated under vacuum. Chromatography of the crude product on silica gel (15 g) using a methanol in dichloromethane elution gradient (2–6% methanol), followed by crystallisation from ethanol, gave the title compound as a colourless solid (1.3 g, 77%), m.p. 182°–184° C. Found: C,60.85; H,6.40; N,18.06. C$_{16}$H$_{20}$N$_4$O$_3$ requires C,60.74; H,6.37; N,17.71%.

Biological activity

The following Table illustrates the in vitro activities for the compounds of the invention.

TABLE

IN VITRO PDE INHIBITORY DATA: SELECTIVITY BETWEEN CALCIUM/CALMODULIN (Ca/CAM)-INDEPENDENT cGMP PDE AND cGMP-INHIBITED cAMP PDE

| EXAMPLE | IC$_{50}$(nM) cGMP | cAMP | SELECTIVITY RATIO |
|---|---|---|---|
| 1 | 97 | >100,000 | >1,030 |
| 2 | 16 | 100,000 | 6,250 |
| 3 | 6.4 | 80,000 | 12,500 |

I claim:

1. A compound of formula (I)

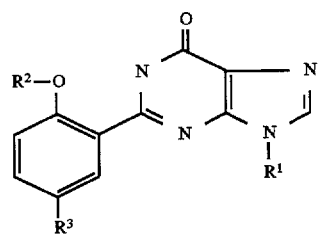

or a pharmaceutically acceptable salt thereof,
wherein R$^1$ and R$^2$ are each independently ethyl or n-propyl;
R$^3$ is H or SO$_2$NR$^4$R$^5$;
and R$^4$ and R$^5$ together with the nitrogen atom to which they are attached form a 4-N-(R$^6$)-1-piperazinyl group; wherein R$^6$ is H or C$_1$–C$_3$ alkyl.

2. A compound of formula (II):
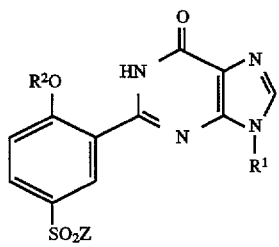
wherein Z is halo, $R^1$ is $C^1$–$C^4$ alkyl and $R^2$ is $C^2$–$C^4$ alkyl.
3. A compound according to claim 2 wherein $R^1$ is n-propyl; $R^2$ is ethyl; and $R^3$ is 1-piperazinylsulphonyl or 4-methyl-1-piperazinylsulphonyl.
4. A compound according to claim 2 wherein Z is chloro.
* * * * *

UNITED STATES PATENT AND TRADEMARK OFFICE
CERTIFICATE OF CORRECTION

PATENT NO. : 5,734,053

DATED : March 31, 1998

INVENTOR(S) : Nicholas Kenneth Terrett

It is certified that error appears in the above-identified patent and that said Letters Patent is hereby corrected as shown below:

At column 10, line 3, delete "claim 2" and insert in place thereof -- claim 1 --.

Signed and Sealed this

Twenty-ninth Day of December, 1998

*Attest:*

BRUCE LEHMAN

*Attesting Officer*   *Commissioner of Patents and Trademarks*